United States Patent
Kwon et al.

(10) Patent No.: US 12,046,937 B2
(45) Date of Patent: Jul. 23, 2024

(54) WIRELESS CHARGER WITH STERILIZATION FUNCTION

(71) Applicant: SOLUM CO., LTD., Yongin-si (KR)

(72) Inventors: Woochan Kwon, Suwon-si (KR); Jaisul Yu, Seoul (KR); Hyung Bong Jeon, Suwon-si (KR)

(73) Assignee: SOLUM CO., LTD., Yongin-si (KR)

( * ) Notice: Subject to any disclaimer, the term of this patent is extended or adjusted under 35 U.S.C. 154(b) by 425 days.

(21) Appl. No.: 17/397,795

(22) Filed: Aug. 9, 2021

(65) Prior Publication Data

US 2022/0123568 A1 Apr. 21, 2022

(30) Foreign Application Priority Data

Oct. 15, 2020 (KR) .................. 10-2020-0133657
May 6, 2021 (KR) .................. 20-2021-0001438

(51) Int. Cl.
*H02J 7/00* (2006.01)
*A61L 2/10* (2006.01)
*H02J 50/12* (2016.01)

(52) U.S. Cl.
CPC ............ *H02J 7/0044* (2013.01); *A61L 2/10* (2013.01); *H02J 7/0047* (2013.01); *H02J 50/12* (2016.02)

(58) Field of Classification Search
CPC .................................................. H02J 7/0044
USPC ........................................................ 320/114
See application file for complete search history.

(56) References Cited

U.S. PATENT DOCUMENTS

| | | | |
|---|---|---|---|
| 10,250,066 B2* | 4/2019 | Jankins | H02J 50/12 |
| 2010/0201311 A1* | 8/2010 | Lyell Kirby | A61L 2/02 |
| | | | 320/108 |
| 2014/0375258 A1* | 12/2014 | Arkhipenkov | H02J 7/0044 |
| | | | 320/108 |
| 2017/0080251 A1* | 3/2017 | Yehezkel | H04M 1/17 |
| 2019/0052104 A1* | 2/2019 | Schlachte | H02J 7/0044 |
| 2019/0099509 A1* | 4/2019 | Martz | A61L 2/24 |
| 2019/0288540 A1* | 9/2019 | Dang | H02J 50/005 |
| 2019/0351082 A1* | 11/2019 | Martz | A61L 2/24 |
| 2022/0045541 A1* | 2/2022 | Kreifeldt | H02J 50/20 |
| 2022/0149656 A1* | 5/2022 | Georgiades | H02J 7/0044 |
| 2022/0305154 A1* | 9/2022 | Hrecznyj | A61L 2/10 |
| 2023/0232871 A1* | 7/2023 | Wu | A61L 2/10 |
| | | | 250/455.11 |

* cited by examiner

*Primary Examiner* — Jerry D Robbins
(74) *Attorney, Agent, or Firm* — Ladas & Parry, LLP

(57) ABSTRACT

A wireless charger with a sterilization function is provided. The wireless charger includes a main body configured to include an internal space opened upward and a seating surface forming a bottom surface of the internal space; a cover configured to be rotatably connected to the main body to open and close the internal space of the main body; an ultraviolet lamp configured to be disposed on the seating surface and a lower surface of the cover, respectively, to irradiate ultraviolet rays into the internal space of the main body; and a transmit coil configured to be disposed inside the cover to transmit energy to an electronic device placed on an upper surface opposing to the lower surface of the cover.

8 Claims, 6 Drawing Sheets

WIRELESS CHARGER WITH STERILIZATION FUNCTION

CROSS-REFERENCE TO RELATED APPLICATION(S)

This application is based on and claims priority under 35 U.S.C. § 119 to Korean Patent Application No. 10-2020-0133657, filed on Oct. 15, 2020, and Korean Patent Application No. 20-2021-0001438, filed on May 6, 2021 in the Korean Intellectual Property Office, the disclosures of which are herein incorporated by reference in their entireties.

BACKGROUND

Field

Apparatuses relate to a wireless charger with a sterilization function, and more particularly, to a wireless charger with a sterilization function that may perform sterilization inside a main body and may wirelessly charge an electronic device placed on an upper surface of a cover for opening or closing the inside of the main body by the cover

Description of the Related Art

Recently, a technology for wirelessly charging a battery of an electronic device without connecting a cable to the electronic device has been developed. In addition, as interest in personal hygiene increases, the need for sterilization of electronic devices used by users for a long time is increasing.

On the other hand, in the conventional wireless charger with a sterilization function, sterilization and charging of the electronic device were simultaneously performed inside a main body. However, there is a problem that the user may not check a charging level of the electronic device disposed inside the main body.

SUMMARY

Embodiments of the disclosure overcome the above disadvantages and other disadvantages not described above. Also, the disclosure is not required to overcome the disadvantages described above, and an embodiment of the disclosure may not overcome any of the problems described above.

The disclosure provides a wireless charger with a sterilization function that may perform sterilization inside a main body and may wirelessly charge an electronic device placed on an upper surface of a cover for opening or closing the inside of the main body by the cover.

According to an embodiment of the disclosure, a wireless charger with a sterilization function includes a main body configured to include an internal space opened upward and a seating surface forming a bottom surface of the internal space; a cover configured to be rotatably connected to the main body to open or close the internal space of the main body; an ultraviolet lamp configured to be disposed on the seating surface and a lower surface of the cover, respectively, to irradiate ultraviolet rays into the internal space of the main body; and a transmit coil configured to be disposed inside the cover to transmit energy to an electronic device placed on an upper surface opposing to the lower surface of the cover.

The main body may include a plurality of protrusions formed to protrude upward from the seating surface.

The seating surface may include an intermediate region that is horizontally disposed; and inclined regions disposed on both sides of the intermediate region and disposed to be inclined downward in a direction away from the intermediate region.

The main body may have a side surface that is inclined so that a lower end is located more outward than an upper end.

The cover may have a side surface that is inclined so that an upper end is located more outward than a lower end.

The cover may include a sealing member protruding from the lower surface of the cover and having a side surface in contact with an inner side surface of the main body when the cover closes the internal space.

The wireless charger may further include a sensor configured to detect whether the cover opens or closes the internal space; and a processor configured to control the ultraviolet lamp to stop the irradiation of ultraviolet rays when it is determined that the internal space is opened based on information received from the sensor.

The main body may include an LED indicator configured to be disposed on a front surface thereof to indicate charging and sterilization states; and a power input port configured to be disposed on a rear surface thereof.

According to diverse embodiments of the disclosure, in the wireless charger with the sterilization function, because the charging object is not located in the internal space of the main body, but is placed on the upper surface of the cover and exposed to the outside, the user may easily check the charging level of the charging object, whether a message has been received, whether a call has been received, and the like.

In addition, when the sterilization of the sterilization object placed on the seating surface of the internal space of the main body is completed, the user may easily take out the sterilization object, which is rotated and erected, from the internal space of the main body by pressing the sterilization object downward toward one of the inclined regions of the seating surface.

In addition, as the side surface of the cover is inclined so that the upper end is located more outward than the lower end, the user may stably grip the inclined side surface of the cover and rotate the cover with a small force, thereby easily opening the internal space of the main body.

BRIEF DESCRIPTION OF THE DRAWINGS

The above and/or other aspects of the disclosure will be more apparent by describing certain embodiments of the disclosure with reference to the accompanying drawings, in which.

DETAILED DESCRIPTION

It should be understood that the embodiments described below are illustratively shown to help understanding of the disclosure, and that the disclosure may be implemented in various modifications, unlike the embodiments described herein. However, in the following description of the disclosure, when it is determined that a detailed description of related known functions or components may unnecessarily obscure the subject matter of the disclosure, the detailed description and specific illustration will be omitted. Further, the accompanying drawings are not illustrated to scale, but sizes of some of components may be exaggerated to help the understanding of the disclosure.

The terms used in the specification and claims have chosen generic terms in consideration of the functions of the disclosure. However, these terms may vary depending on the intentions of the artisan skilled in the art, legal or technical interpretation, and emergence of new technologies. In addition, some terms are arbitrarily chosen by the applicant. These terms may be interpreted as meanings defined in the specification, and may also be interpreted based on the general contents of the specification and common technical knowledge in the art without specific term definitions.

In the disclosure, an expression "have", "may have", "include", "may include", or the like, indicates an existence of a corresponding feature (for example, a numerical value, a function, an operation, a component such as a part, or the like), and does not exclude an existence of an additional feature.

In addition, in the specification, components necessary for description of each embodiment of the disclosure are described, and thus are not necessarily limited thereto. Therefore, some components may be changed or omitted, and other components may be added. In addition, the components may be disposed to be distributed in different independent apparatuses.

Further, hereinafter, embodiments of the disclosure will be described in detail with reference to the accompanying drawings and the contents described in the accompanying drawings, but the disclosure is not limited or restricted to the embodiments.

Hereinafter, the disclosure will be described in more detail with reference to the accompanying drawings.

Figure 1:
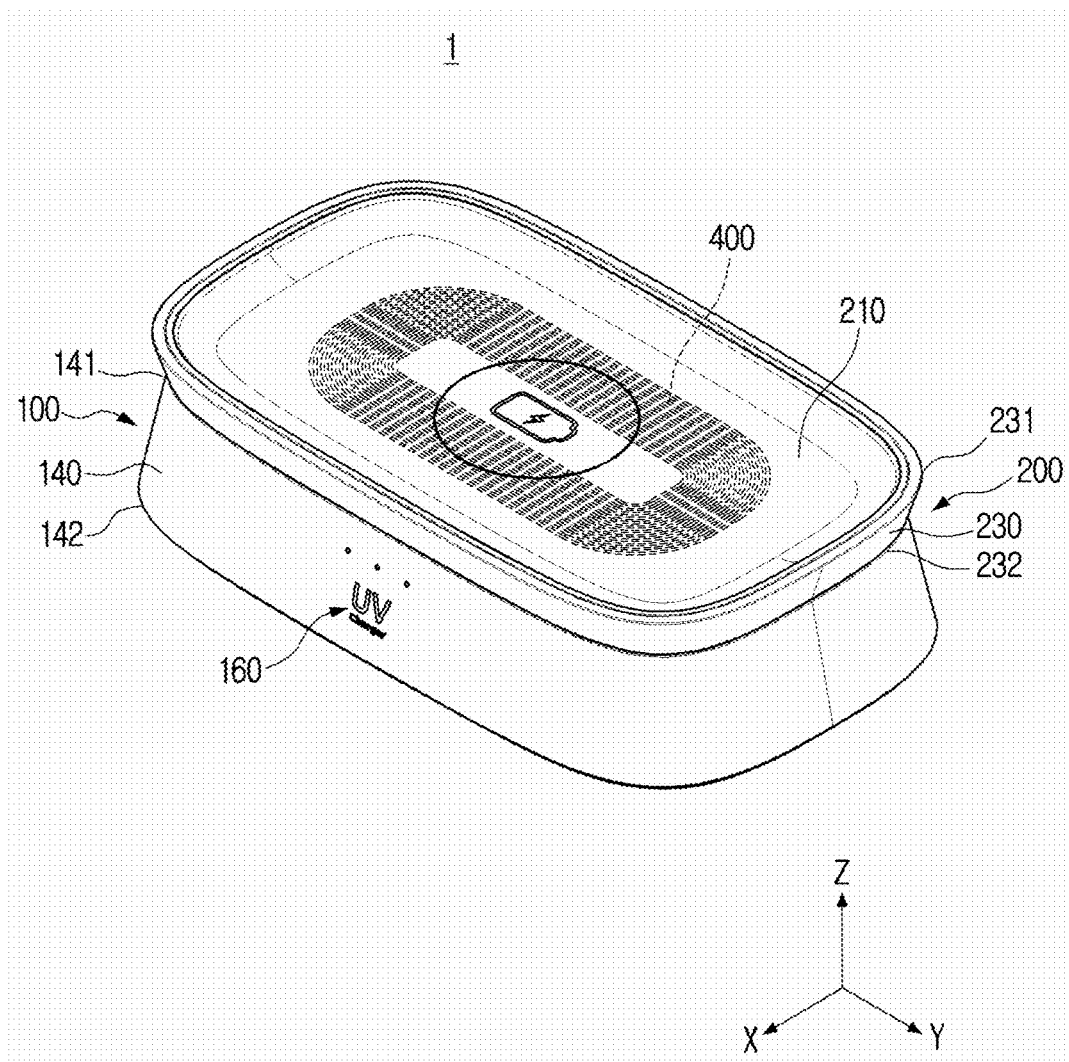
FIG. 1 is a front perspective view of a wireless charger with a sterilization function according to an embodiment of the disclosure.
Figure 2:
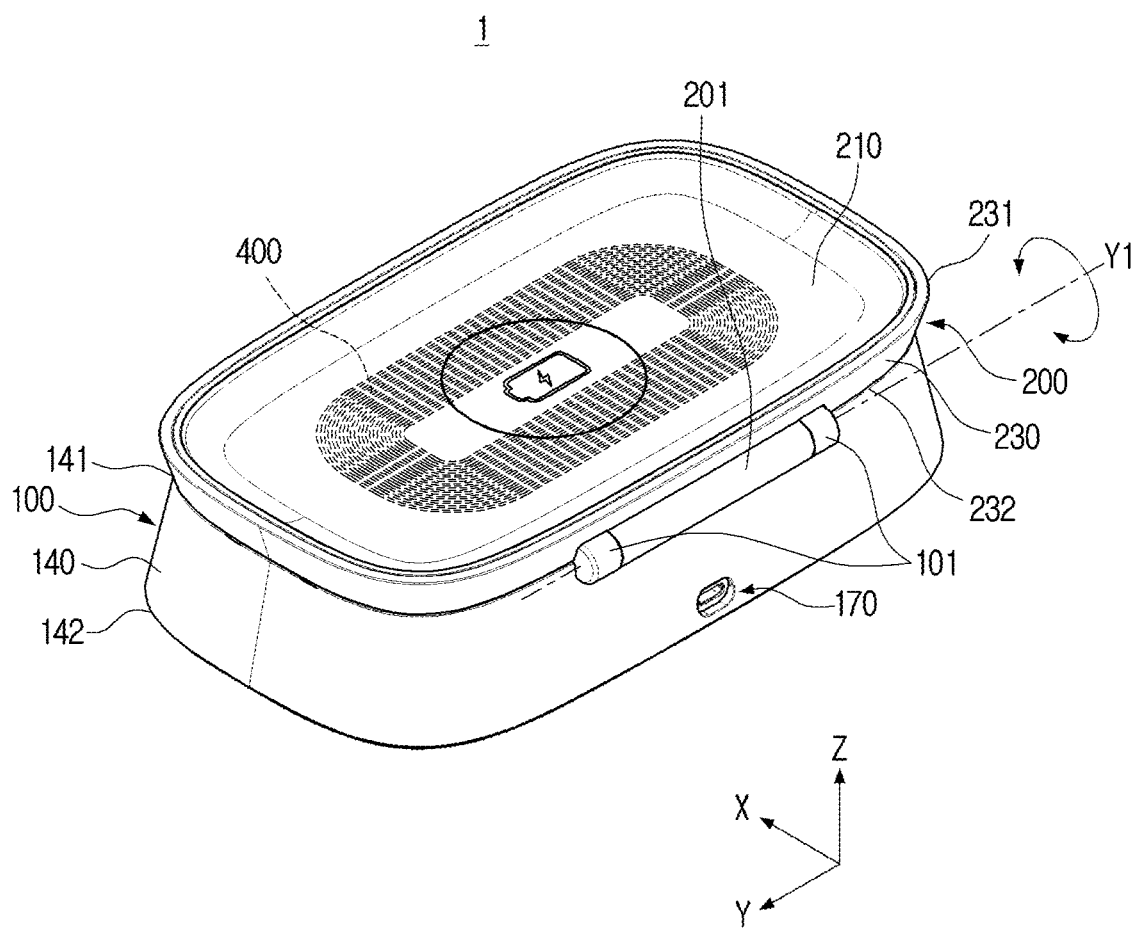
FIG. 2 is a rear perspective view of the wireless charger of FIG. 1.
Figure 3:
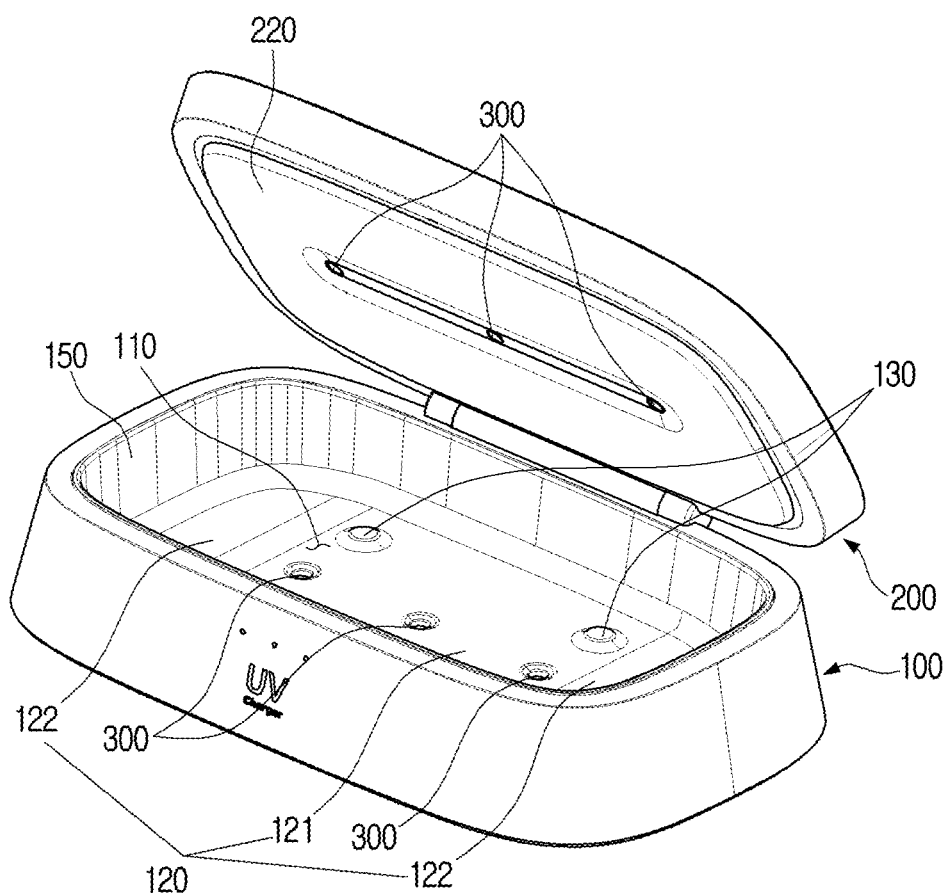
FIG. 3 is a view illustrating a state in which a cover of the wireless charger of FIG. 1 is opened.

FIG. 1 is a front perspective view of a wireless charger with a sterilization function according to an embodiment of the disclosure. FIG. 2 is a rear perspective view of the wireless charger of FIG. 1. FIG. 3 is a view illustrating a state in which a cover of the wireless charger of FIG. 1 is opened.

Referring to FIGS. 1 to 3, a wireless charger 1 with a sterilization function according to an embodiment of the disclosure may include a main body 100, a cover 200, an ultraviolet lamp 300, and a transmit coil 400.

The main body 100 may include an internal space 110 opened upward (+Z direction) and a seating surface 120 forming a bottom surface of the internal space 110.

The cover 200 may be rotatably connected to the main body 100 to open or close the internal space 110 of the main body 100.

In detail, a second hinge shaft 201 of the cover 200 may be disposed between first hinge shafts 101 of the main body 100, and may be rotatably connected to the first hinge shafts 101 of the main body 100. The first and second hinge shafts 101 and 201 may be disposed in parallel with each other to define a rotation shaft parallel to a Y1 axis. Accordingly, the cover 200 may be rotated with respect to the main body 100 based on the Y1 axis to open or close the internal space 110 of the main body 100.

When the cover 200 rotates by a preset angle (e.g., 30 degrees, 60 degrees, 90 degrees, etc.) with respect to the main body 100, the cover 200 may be fixed so that the rotation angle is maintained. Accordingly, because the user does not feel that the cover 200 fixed at a specific rotation angle is loose, convenience of use may be increased.

The ultraviolet lamp 300 may be disposed on the seating surface 120 and a lower surface 220 of the cover 200, respectively, to irradiate ultraviolet rays into the internal space 110 of the main body 100.

The ultraviolet lamp 300 may irradiate UV-C having a wavelength of 200 nm or more and 280 nm or less, rather than general UV having a wavelength of 100 nm or more and 200 nm or more. Accordingly, the ultraviolet lamp 300 has a sustaining power of 10 times or more as compared to a lamp irradiating the general UV, and may be environmentally friendly because it does not use mercury.

A total of six UV lamps 300 may be provided, three UV lamps may be disposed on the seating surface 120, and three UV lamps may be disposed on the lower surface 220 of the cover 200, but the number of UV lamps is not limited thereto. The plurality of ultraviolet lamps 300 may be disposed in a length direction of the wireless charger 1, that is, parallel to a Y-axis.

Because a sterilization object placed in the internal space 110 of the main body 100 is irradiated with ultraviolet rays from the upper and lower sides, the sterilization object may be uniformly sterilized over the entire region. The entire region of the sterilization object may be uniformly sterilized with only about 10 minutes of sterilization, but the sterilization time is not limited thereto.

The sterilization object placed in the internal space 110 of the main body 100 may be a mobile phone, a mask, and cosmetic utensils, but is not limited thereto.

On the other hand, the components forming the internal space 110 of the main body 100 may have a surface formed of a metal material. Accordingly, because the ultraviolet rays irradiated by the ultraviolet lamp 300 collides with the metal surface and are continuously reflected, it is possible to uniformly sterilize the entire region of the sterilization object, and the sterilization efficiency may be improved.

The transmit coil 400 may be disposed inside the cover 200 to transmit energy to an electronic device placed on the upper surface 210 of the cover 200 opposing to the lower surface 220 of the cover 200.

In detail, when a current flows through the transmit coil 400 to generate an electromagnetic field, an induced current flows through a receive coil in the electronic device, so that the electronic device may be wirelessly charged.

A charging object placed on the upper surface 210 of the cover 200 may be a mobile phone and a wireless earphone, but is not limited thereto.

Because the charging object is not located in the internal space 110 of the main body 100, but is placed on the upper surface 210 of the cover 200 and exposed to the outside, the user may easily check a charging level of the charging object, whether a message has been received, whether a call has been received, and the like.

A side surface 230 of the cover 200 may be inclined so that an upper end 231 thereof is located more outward than a lower end 232 thereof. That is, an end surface of the cover 200 may have a trapezoidal shape in which an upper side is longer than a lower side.

As the side surface 230 of the cover 200 is inclined as described above, the user may stably grip the inclined side surface 230 of the cover 200 with a finger. In addition, as the user moves the finger vertically upward (+Z direction) while gripping the side surface 230 of the cover 200, the user may easily open the internal space 110 of the main body 100 by rotating the cover 200 with a small force.

The main body 100 may include an LED indicator 160 disposed on a front surface to indicate charging and sterilization states, and a power input port 170 disposed on a rear surface.

The LED indicator 160 may irradiate light of various colors forward to indicate various states corresponding to each color of the light (e.g., ON/OFF state, charging state, fully charged state, sterilization state, sterilization completion state, etc.). Accordingly, the user may intuitively check what kind of operation the wireless charger 1 is currently performing.

The wireless charger 1 may receive external power through the power input port 170 disposed on the rear surface. Accordingly, the front surface of the wireless charger 1 may have a neat appearance.

The power input port 170 may be a USB-C type, but is not limited thereto. Electrical energy supplied through the power input port 170 may be transmitted to the LED indicator 160, the ultraviolet lamp 300, and the transmit coil 400.

The LED indicator 160 may also serve as a touch-type switch. That is, the user may control an operation of the wireless charger 1 by touching the LED indicator 160. Accordingly, because the LED indicator 160, which is the touch-type switch, not a mechanical switch, is disposed on the front surface of the main body 100, the front surface of the main body 100 may have a smooth and neat appearance without a step.

A side surface 140 of the main body 100 may be inclined so that a lower end 142 thereof is located more outward than an upper end 141 thereof. That is, an end surface of the side surface of the main body 100 may have a trapezoidal shape in which a lower side is longer than an upper side.

Accordingly, a user looking down at the wireless charger 1 may easily checks the LED indicator 160 disposed on the inclined side surface 140 of the main body 100 to check an operating state of the wireless charger 1.

The wireless charger 1 does not have an angled portion as a whole, and may be designed in a streamlined design. Accordingly, the wireless charger 1 may have a luxurious appearance like a jewelry box as an interior element.

Figure 4:
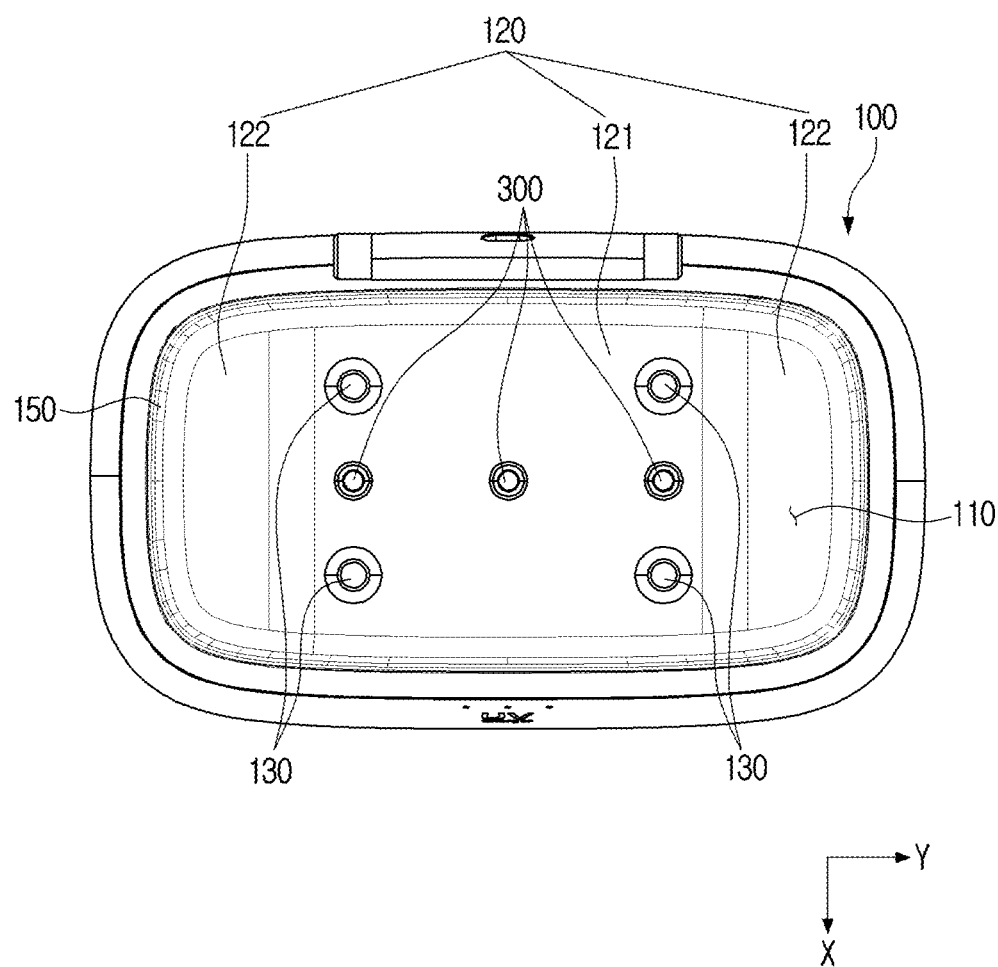
FIG. 4 is a top view illustrating an internal space of a main body.

FIG. 4 is a top view illustrating an internal space of a main body.

Referring to FIG. 4, the main body 100 may include a plurality of protrusions 130 protruding upward from the seating surface 120.

That is, the sterilization object disposed in the internal space 110 of the main body 100 may be supported by the plurality of protrusions 130. Accordingly, because the sterilization object does not come into direct contact with the ultraviolet lamps 300 disposed on the seating surface 120, it is possible to prevent the sterilization object from being unintentionally heated by the ultraviolet lamps 300.

The plurality of protrusions 130 may be provided in four and may be arranged in a lattice form, but the number or arrangement of the protrusions is not limited thereto.

The plurality of protrusions 130 are formed of a soft rubber material having a high coefficient of friction, and thus, it is possible to prevent the sterilization object placed on the protrusions 130 from slipping or being damaged unintentionally.

The seating surface 120 may include an intermediate region 121 that is horizontally disposed and inclined regions 122 disposed on both sides of the intermediate region 121 and disposed to be inclined downward in a direction away from the intermediate region 121.

When the sterilization of the sterilization object placed on the seating surface 120 is completed, the user may press the sterilization object downward toward one inclined region 122 of the two inclined regions 122.

Accordingly, the sterilization object is rotated and erected so that one end thereof is close to any one inclined area 122, and the user may easily take out the sterilization object that has been sterilized from the internal space 110 of the main body 100.

Figure 5:
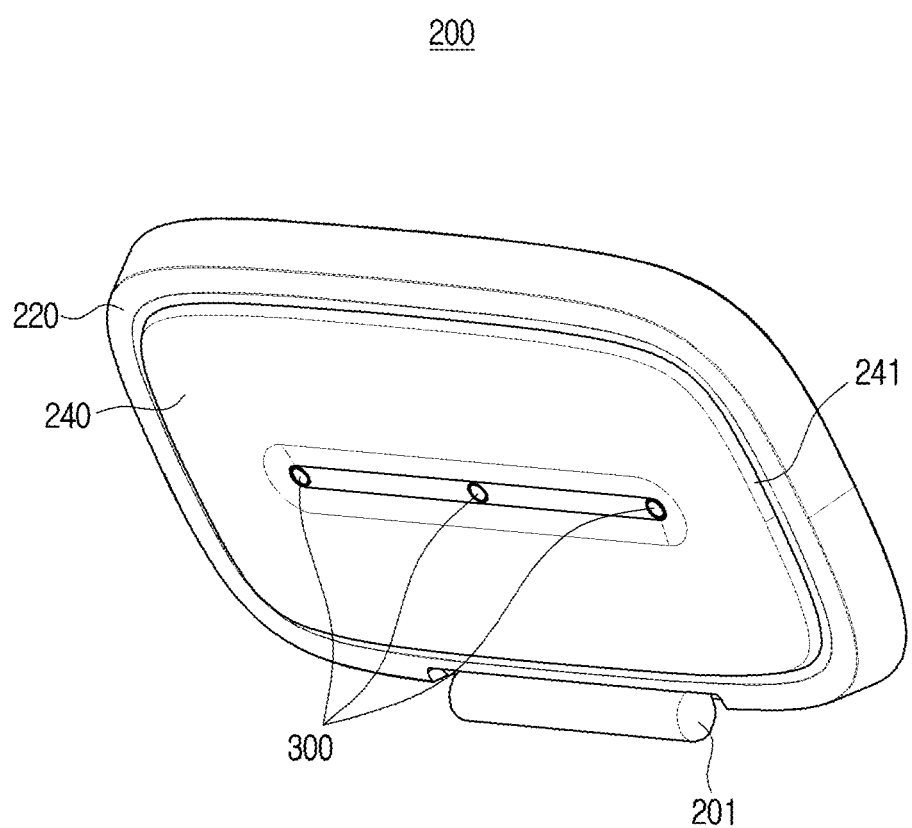
FIG. 5 is a front perspective view of the cover.

FIG. 5 is a front perspective view of the cover.

The cover 200 may include a sealing member 240 protruding from the lower surface 220 of the cover 200 and having a side surface 241 in contact with an inner side surface 150 of the main body 100 when the cover 200 closes the internal space 110.

The sealing member 240 may rotate together with the cover 200 to be inserted into the internal space 110 of the main body 100. The sealing member 240 may be formed of a metal material capable of reflecting ultraviolet rays.

In a state in which the cover 200 closes the internal space 110, because the side surface 241 of the sealing member 240 is in contact with the inner side surface 150 of the main body 100, a phenomenon in which ultraviolet rays are unintentionally leaked to the outside may be prevented.

Figure 6:
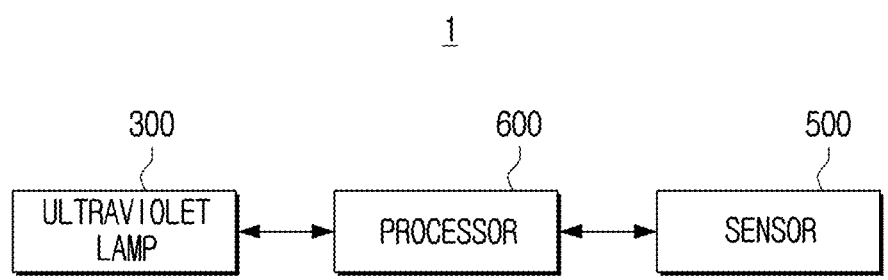
FIG. 6 is a block diagram for explaining the wireless charger according to an embodiment of the disclosure.

FIG. 6 is a block diagram for explaining the wireless charger according to an embodiment of the disclosure.

Referring to FIG. 6, the wireless charger 1 according to an embodiment of the disclosure may further include a sensor 500 and a processor 600.

The sensor 500 may detect whether the cover 200 opens or closes the internal space 110. For example, the sensor 500 may detect whether the cover 200 opens or closes the internal space 110 by detecting the rotation angle of the cover 200 or detecting whether the cover 200 and the main body 100 are in contact.

If it is determined that the internal space 110 is opened based on information received from the sensor 500, the processor 600 may control the ultraviolet lamp 300 to stop the irradiation of ultraviolet rays.

Accordingly, because the ultraviolet lamp 300 does not irradiate ultraviolet rays when the cover 200 opens the internal space 110, a phenomenon in which ultraviolet rays are unintentionally leaked to the outside of the internal space 110 may be prevented.

In the above, the embodiment of the disclosure has been shown and described, but the disclosure is not limited to the specific embodiment described above, and anyone with ordinary skill in the art to which the disclosure pertains can make various modifications without departing from the gist of the disclosure as claimed in the claims, and such modifications are intended to be within the scope of the claims.

What is claimed is:

1. A wireless charger with a sterilization function, the wireless charger comprising:
   a main body configured to include an internal space opened upward and a seating surface forming a bottom surface of the internal space;
   a cover configured to be rotatably connected to the main body to open or close the internal space of the main body;
   an ultraviolet lamp configured to be disposed on the seating surface and a lower surface of the cover, respectively, to irradiate ultraviolet rays into the internal space of the main body; and a transmit coil configured to be disposed inside the cover to transmit energy to an electronic device placed on an upper surface opposing to the lower surface of the cover, wherein the wireless charger is configured to perform sterilization in a first area adjacent to the lower surface of the cover and perform charging in a second area adjacent to the upper surface of the cover.

2. The wireless charger as claimed in claim 1, wherein the main body includes a plurality of protrusions formed to protrude upward from the seating surface.

3. The wireless charger as claimed in claim 1, wherein the seating surface includes:
   an intermediate region that is horizontally disposed; and
   inclined regions disposed on both sides of the intermediate region and disposed to be inclined downward in a direction away from the intermediate region.

4. The wireless charger as claimed in claim 1, wherein the main body has a side surface that is inclined so that a lower end is located more outward than an upper end.

5. The wireless charger as claimed in claim 1, wherein the cover has a side surface that is inclined so that an upper end is located more outward than a lower end.

6. The wireless charger as claimed in claim 1, wherein the cover includes a sealing member protruding from the lower surface of the cover and having a side surface in contact with an inner side surface of the main body when the cover closes the internal space.

7. The wireless charger as claimed in claim 1, further comprising:
   a sensor configured to detect whether the cover opens or closes the internal space; and
   a processor configured to control the ultraviolet lamp to stop the irradiation of ultraviolet rays when it is determined that the internal space is opened based on information received from the sensor.

8. The wireless charger as claimed in claim 1, wherein the main body includes:
   an LED indicator configured to be disposed on a front surface thereof to indicate charging and sterilization states; and
   a power input port configured to be disposed on a rear surface thereof.

\* \* \* \* \*